United States Patent [19]

Trese et al.

[11] Patent Number: 5,304,118
[45] Date of Patent: Apr. 19, 1994

[54] METHOD FOR PERFORMING A VITRECTOMY ON AN EYE

[76] Inventors: Michael T. Trese, 3675 Franklin Rd., Bloomfield Hills, Mich. 48302; George A. Williams, 1009 Three Mile Dr., Grosse Pointe Park, Mich. 48230; Michael Hartzer, 300 Arizona Ave., Rochester Hills, Mich. 48309

[21] Appl. No.: 991,253
[22] Filed: Dec. 16, 1992
[51] Int. Cl.⁵ .......................................... A61M 31/00
[52] U.S. Cl. ..................................... 604/51; 604/290; 604/294; 128/898
[58] Field of Search .................. 604/51, 22, 27, 290, 604/294; 128/898

[56] References Cited

U.S. PATENT DOCUMENTS

| | | | |
|---|---|---|---|
| 4,299,227 | 11/1981 | Lincoff | 128/898 X |
| 4,328,803 | 5/1982 | Pape | 128/898 X |
| 4,764,466 | 8/1988 | Suyama et al. | 435/174 |
| 4,853,224 | 8/1989 | Wong | 424/427 |
| 4,997,652 | 3/1991 | Wong | 424/428 |
| 5,002,571 | 3/1991 | O'Donnell, Jr. et al. | 623/6 |
| 5,047,008 | 9/1991 | de Juan, Jr. et al. | 604/22 |
| 5,066,276 | 11/1991 | Wang | 604/51 |
| 5,120,307 | 6/1992 | Wang | 604/51 |
| 5,178,635 | 1/1993 | Gwon et al. | 623/4 |
| 5,182,259 | 1/1993 | Kita | 604/290 X |
| 5,244,799 | 9/1993 | Anderson | 435/240.23 |

Primary Examiner—Randall L. Green
Assistant Examiner—Mary Beth D. Jones
Attorney, Agent, or Firm—Gifford, Groh, Sprinkle, Patmore and Anderson

[57] ABSTRACT

A method for performing a vitrectomy on an eye is disclosed for removing the vitreous humor from the eye. The method comprises the first step of introducing plasmin into the vitreous humor in order to induce a posterior vitreous detachment. Thereafter, the vitreous is removed by conventional methods and replaced with a sterile saline solution.

7 Claims, 1 Drawing Sheet

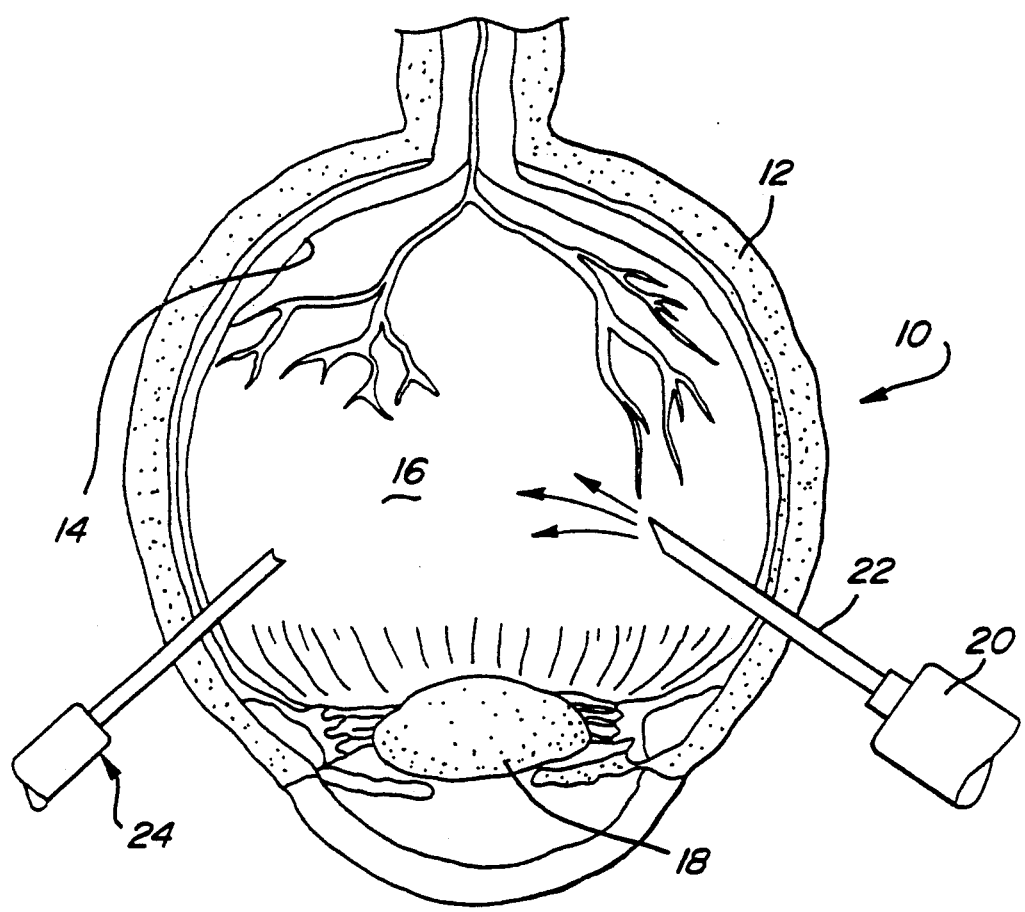

METHOD FOR PERFORMING A VITRECTOMY ON AN EYE

BACKGROUND OF THE INVENTION

I. Field of the Invention

The present invention relates generally to medical procedures and, more particularly, to a medical procedure for performing a vitrectomy on an eye or causing posterior vitreous detachment.

II. Description of the Prior Art

In order to treat certain medical diseases and dysfunctions in the eye, and especially human eyes, it is necessary to perform a vitrectomy on the eye. As is well known, a vitrectomy involves the removal of the vitreous humor from the eye and the replacement of the vitreous humor by a sterile saline solution.

The vitreous humor or vitreous is a semi-solid material (gel) having a jello-like consistency. In order to remove the vitreous from the eye, the vitreous is conventionally mechanically removed from the eye while simultaneously replacing the removed vitreous with a saline solution to prevent collapse of the eye.

One difficulty in performing a vitrectomy is that the vitreous exhibits a relatively strong adhesion to the retina of the eye. Mechanical removal of the vitreous from the retina of the eye can result in scarring, tearing and other damage to the retina. Such retinal damage, of course, is highly undesirable since such damage may compromise the patient's vision following the vitrectomy.

SUMMARY OF THE PRESENT INVENTION

The present invention provides a method for performing a vitrectomy which overcomes the above mentioned disadvantages of the previously known methods.

In brief, in accordance with the method of the present invention, human plasmin is introduced into the vitreous prior to removing the vitreous from the eye, at least in the retinal region. It has been found that, after a relatively short time period, the plasmin induces posterior vitreous detachment from the retina so that removal of the vitreous from the eye can be accomplished with only minimal risk of retinal damage during the vitrectomy.

Although the plasmin can be introduced into the eye simultaneous with the removal of the vitreous, in the preferred embodiment of the invention, the plasmin is injected into the vitreous and allowed to induce the posterior vitreous detachment for between five and sixty minutes before removal of the vitreous from the eye.

BRIEF DESCRIPTION OF THE DRAWING

A better understanding of the present invention will be had upon reference to the following detailed description when read in conjunction with the accompanying drawing which is a cross sectional view of an eye undergoing a vitrectomy in accordance with the method of the present invention.

DETAILED DESCRIPTION OF PREFERRED EMBODIMENTS OF THE PRESENT INVENTION

With reference to the drawing, an eye 10, such as a human eye, is thereshown in which the sclera 12 forms a generally spherical outer body for the eye 10. A retina 14 extends along the inside rear surface of the sclera 12 while vitreous humor or vitreous 16 fills the volume of the sclera 12 posteriorly of the natural eye lens 18.

In a vitrectomy, the vitreous 16 is removed from the eye 10 and replaced by a sterile saline solution. In accordance with the present invention, plasmin 20 is first introduced into the vitreous 16 by any conventional means, such as through a hypodermic needle 22. It has been found that after a relatively short period, for example five to sixty minutes following the introduction of the plasmin into the vitreous 16, the plasmin 20 induces a posterior vitreous detachment, i.e. detachment of the vitreous 16 from the retina 14.

Following posterior vitreous detachment, the vitreous 16 is removed from the eye 10 by conventional means 24. Furthermore, due to the separation between the vitreous 16 and the retina 14, the risk of damage from the vitreous removing means 24 to the retina 14 is minimized since scraping or other contact between the vitreous removing means 24 and retina 14 is either minimized or altogether eliminated.

Although the precise amount of plasmin necessary to induce the posterior vitreous detachment is unknown, it has been found that the introduction of between one unit and three units of plasmin into the vitreous 16 is sufficient to induce posterior vitreous detachment.

Although in the preferred form of the invention, the plasmin 20 is introduced into the vitreous 16 and the vitreous 16 then removed after a predetermined time period, alternatively the plasmin 20 can be introduced into the vitreous 16 simultaneously with the removal of the vitreous 16 from the eye 10. Since it is necessary to introduce a sterile saline solution into the eye 10 to replace the removed vitreous 16, the plasmin can also be intermixed with the sterile saline solution.

Having described my invention, many modifications thereto will become apparent to those skilled in the art to which it pertains without deviation from the spirit of the invention as defined by the scope of the appended claims.

We claim:

1. A method of performing a vitrectomy on an eye having vitreous humor comprising the steps of:
    introducing plasmin into the vitreous humor in an amount sufficient to induce posterior vitreous detachment,
    thereafter removing the vitreous humor.

2. The invention as defined in claim 1 wherein said removing step comprises the step of mechanically removing said vitreous humor from said eye.

3. The invention as defined in claim 2 wherein said plasmin introducing step and said vitreous humor removing step are carried out simultaneously.

4. The invention as defined in claim 3 and further comprising the step of introducing a sterile solution into said eye to replace the vitreous humor as it is removed from the eye, and wherein said plasmin is contained within said sterile solution.

5. The invention as defined in claim 1 and further comprising the step of waiting a predetermined time period after introduction of said plasmin into said eye before removing said vitreous humor.

6. The invention as defined in claim 5 wherein said predetermined time period is in excess of five minutes.

7. The invention as defined in claim 1 wherein said introducing step further comprises the step of introducing between one unit and three units into the vitreous.

* * * * *